(12) United States Patent
Gallego et al.

(10) Patent No.: US 10,327,660 B2
(45) Date of Patent: Jun. 25, 2019

(54) HEALTH MONITORING

(75) Inventors: Angela Gallego, Oxford (GB); Rebecca Weir, Oxford (GB); Keith Errey, Oxford (GB)

(73) Assignee: Isansys Lifecare Limited, Abingdon, Oxfordshire (GB)

(*) Notice: Subject to any disclaimer, the term of this patent is extended or adjusted under 35 U.S.C. 154(b) by 1420 days.

(21) Appl. No.: 13/983,590

(22) PCT Filed: Feb. 3, 2012

(86) PCT No.: PCT/GB2012/050244
§ 371 (c)(1),
(2), (4) Date: Oct. 14, 2013

(87) PCT Pub. No.: WO2012/104657
PCT Pub. Date: Aug. 9, 2012

(65) Prior Publication Data
US 2014/0031663 A1    Jan. 30, 2014

(30) Foreign Application Priority Data
Feb. 3, 2011    (GB) .................................... 1101857.9

(51) Int. Cl.
*A61B 5/0408* (2006.01)
*H05K 5/02* (2006.01)
(Continued)

(52) U.S. Cl.
CPC ...... *A61B 5/04325* (2013.01); *A61B 5/04085* (2013.01); *A61B 5/6801* (2013.01);
(Continued)

(58) Field of Classification Search
CPC ...... A61B 5/6801; H05K 13/00; H05K 13/08; H05K 5/0256; H01R 43/00
(Continued)

(56) References Cited

U.S. PATENT DOCUMENTS 5,500,635 A * 3/1996 Mott .................... A43B 1/0072
                                                310/311
5,749,365 A * 5/1998 Magill ................. A61B 5/0008
                                                128/903
(Continued)

FOREIGN PATENT DOCUMENTS

EP    2 438 854 A2    4/2012
GB    2425181 A    10/2006
(Continued)

OTHER PUBLICATIONS

US Food and Drug Administration, "Reprocessing of Single-Use Devices > Frequently Asked Questions" at http://www.fda.gov/MedicalDevices/DeviceRegulationandGuidance/ReprocessingofSingle-UseDevices/ucm121093.htm (2001), accessed May 2014.*
(Continued)

*Primary Examiner* — Lee S Cohen
*Assistant Examiner* — Erin M Cardinal
(74) *Attorney, Agent, or Firm* — Eversheds Sutherland (US) LLP

(57) ABSTRACT

An electrode assembly for making electrocardiogram measurements includes a substrate and at least two electrodes. The substrate includes at least one electronic item sealed therewithin and is laminated or otherwise constructed so as to facilitate removal of the electronic item from the substrate prior to disposal. The electronic item may therefore be re-used in the manufacture of new electrode assemblies.

14 Claims, 8 Drawing Sheets

(51) Int. Cl.
  *A61B 5/0432* (2006.01)
  *A61B 5/00* (2006.01)
  *B23P 6/00* (2006.01)

(52) U.S. Cl.
  CPC ........ *H05K 5/0256* (2013.01); *A61B 5/04087* (2013.01); *A61B 2562/08* (2013.01); *B23P 6/00* (2013.01); *Y10T 29/4913* (2015.01)

(58) Field of Classification Search
  USPC ..... 29/825, 402.01, 402.03, 402.04; 128/898
  See application file for complete search history.

(56) References Cited

U.S. PATENT DOCUMENTS

| | | | | |
|---|---|---|---|---|
| 6,128,521 | A * | 10/2000 | Marro | A61B 5/04026 600/383 |
| 6,605,046 | B1 * | 8/2003 | Del Mar | A61B 5/04085 600/507 |
| 2005/0245839 | A1 * | 11/2005 | Stivoric | G06F 19/3418 600/549 |
| 2007/0038883 | A1 | 2/2007 | Gerder et al. | |
| 2008/0275327 | A1 * | 11/2008 | Faarbaek | A61B 5/0002 600/382 |
| 2008/0278336 | A1 | 11/2008 | Ortega et al. | |
| 2009/0073991 | A1 * | 3/2009 | Landrum | A61B 5/0006 370/400 |
| 2009/0076336 | A1 * | 3/2009 | Mazar | A61B 5/0402 600/300 |
| 2009/0076340 | A1 | 3/2009 | Libbus et al. | |
| 2009/0076345 | A1 * | 3/2009 | Manicka | A61B 5/0205 600/301 |
| 2009/0154523 | A1 * | 6/2009 | Kim | G01K 13/002 374/141 |
| 2011/0028822 | A1 | 2/2011 | Beck | |
| 2011/0144470 | A1 * | 6/2011 | Mazar | A61B 5/04085 600/391 |
| 2012/0071742 | A1 * | 3/2012 | Medina | A61B 5/14552 600/344 |
| 2012/0089001 | A1 | 4/2012 | Bishay et al. | |
| 2013/0079618 | A1 * | 3/2013 | Sandmore | A61B 5/0478 600/393 |
| 2013/0317333 | A1 * | 11/2013 | Yang | A61B 5/00 600/372 |

FOREIGN PATENT DOCUMENTS

| | | |
|---|---|---|
| JP | 2004033468 | 2/2004 |
| JP | 2010259679 | 11/2010 |
| WO | 2005/041768 A1 | 5/2005 |
| WO | 2006/094513 A2 | 9/2006 |
| WO | 2009/036306 A1 | 3/2009 |
| WO | 2009/055397 A2 | 4/2009 |
| WO | 2010/102310 A2 | 9/2010 |

OTHER PUBLICATIONS

Kwakye, et al. "Commentary: A Call to Go Green in Health Care by Reprocessing Medical Equipment" Academic Med. vol. 85(3) pp. 398-399 (2010).*

Scientific Committee on Emerging and Newly Identified Health Risks, "The Safety of Reporcesssed Medical Devices Marketed for Single-Use" (2010).*

IMEC, Title: Packaging and Integration Technology for Wearable & Implantable Application, IMEC Scientific Report 2010, Aug. 1, 2011.

R. Carta, et al.; Title: Design & Implementation of Advanced System sin a Flexible-Stretchable Technology for Biomedical Applications. Sens. Actuators A: Phys. (2009).

J. Vanfleteren; Title: Flexible & Stretchable Circuit, IMEC, Euripedes Forum 2010 Paris, Sep. 30-Oct. 1, 2010.

* cited by examiner

HEALTH MONITORING

TECHNICAL FIELD

This invention relates to devices which allow monitoring of the vital signs of a subject, particularly although not exclusively monitoring a subject's cardiac rhythm.

BACKGROUND OF THE INVENTION

Wireless electrocardiogram (ECG) monitors, which are placed on a patient to permit the remote monitoring of cardiac rhythm are known e.g. from U.S. Pat. No. 3,943,918. It is also known to provide wireless heart rate monitors which are held against the patient by a chest strap. Not only do such devices tend to be heavy and bulky but the degree of contact with the skin is generally poor and prone to motion artefacts. Moreover the need for a chest strap to be fitted around the subject means that they may not be suitable in trauma situations are where the subject is physically injured or disabled. The Applicant has devised an improved arrangement which aims to alleviate at least some of the shortcomings of known devices.

SUMMARY OF THE INVENTION

When viewed from a first aspect the present invention provides an electrode assembly for taking electrocardiogram measurements, the assembly comprising a substrate, at least two electrodes for making electrical connection to the skin of a mammalian subject, and self-adhesive means for attaching the substrate to the subject, wherein the substrate incorporates data processing means electrically connected to at least one of the electrodes by means of an extendible electrical connection.

Thus it will be seen by those skilled in the art that in accordance with the invention a self-contained ECG electrode assembly is provided which may be attached to the body of a human or animal subject such that an extendible electrical connection between one or both of the electrodes and the data processing circuitry allows relative movement, particularly axial movement, between the electrodes and the rest of the assembly without compromising the integrity of the electrical connection. This is beneficial in allowing a large range of movement of the subject whilst minimising problems associated with the electrode(s) becoming detached or giving inaccurate results as a result of motion artefacts such as electrical noise being introduced by movement of the electrode relative to the subject's body. Furthermore, because the electrical connection to one or both of the electrodes is extendible the electrodes are able to "float" relative to the substrate and move with the body without applying a mechanical stress to the electrical connection that could damage its integrity.

In a set of preferred embodiments, the substrate is elongate—e.g. having a maximum dimension at least twice that of its minimum dimension. Preferably a first one of the electrodes and the data processing means are provided at respective opposite ends of the substrate—defined as the electrode and data processing means being disposed in different halves of the assembly if the substrate is bisected along its longest axis. Preferably a second one of the electrodes is provided on the other end of the substrate to the first electrode, i.e. in the other half of the substrate to the first electrode, and is also electrically connected to the data processing means. The second electrode might be provided close to or directly beneath the data processing means such that a extendible connection between them is not required. An advantage of the data processing means being provided adjacent to or above one of the electrodes is that together they can provide mechanical support for one another. However in another set of embodiments the electrodes may be provided at opposite ends of the substrate with the data processing means provided therebetween. Such embodiments may use more than one extendible connection.

The extendible connection between at least one of the electrodes and the data processing means is preferably such as to allow flexibility in all directions. In a convenient set of embodiments, the or each extendible connection comprises a wire laid out in a serpentine configuration to permit extension and compression along its main axis (e.g. the axis joining the two ends of the wire) as well as flexibility in both dimensions away from the axis. The substrate is preferably made of a flexible material. The flexible material is chosen so as to have an optimal elasticity to match movements of a mammalian, especially human, body. In one exemplary set of embodiments, the substrate is made of medical grade polyurethane. In a set of embodiments, the substrate comprises a laminated structure which has the data processing means, and optionally also the extendible electrical connection(s), embedded between a pair of layers thereof.

The data processing means conveniently comprises an electronic memory for temporary or longer term storage of data therein. The memory could be used to permit periodic downloading of data when the electrode assembly is in the presence of, or connected to a suitable reader, so that real-time communication is not necessary. In a preferred set of embodiments, the electrode assembly comprises a wireless transmitter for transmitting data to a suitable receiver. This could allow the periodic downloading of data referred to above, but is more preferably configured to permit the regular, frequent transmission of data. In a set of preferred embodiments, the wireless transmitter comprises a radio transmitter. An example of a suitable radio transmitter is the ANT wireless transceiver designated AP2 which is available from Nordic Semiconductor ASA. Although the ANT wireless protocol is one preferred low power protocol that employs relatively low data rates, the wireless transmitter may employ any suitable protocol for data transmission. For example, the wireless transmitter may use Bluetooth™ or Bluetooth Low Energy™ technology.

The electrode assembly could be powered in a number of different ways, but in a set of embodiments it comprises a battery to provide power. The battery is conveniently provided in direct contact with the data processing circuitry, thereby obviating the need to provided interconnection, but this is not essential.

In a set of preferred embodiments, the substrate is configured so as to allow disconnection and removal of the data processing circuitry and the battery. This allows partial recycling of the electrode assembly by allowing these components, especially the data processor, to be re-used. The battery may be recharged or replaced. This is not only cost-effective since these components are relatively expensive, but it also avoids the need to dispose of them in an environmentally sensitive manner. The battery and circuitry could, for example, be conveniently arranged in a pocket between two layers of the laminated substrate and connected to the extendible electrical connection and/or electrodes by means of a frangible or other separable connection. This would then allow the substrate to be partially ripped apart to allow access to the aforementioned pocket and the battery/circuitry to be removed from the pocket by tugging. The extendible electrical connection(s) may be removed with the data processing means or it/they may remain in the substrate to be discarded. This be dictated by the physical design of the device.

The electrodes are preferably provided by self-adhesive electrode pads of the type well known per se mounted to the substrate. Such electrode pads may thus also provide the self-adhesive means for attaching the substrate to the subject's body.

It will be appreciated that by having the substrate connected to the self-adhesive electrode pad(s) allows for easy regulatory compliance since standard, pre-approved electrode pads may be employed and it is then not necessary for any other part of the electrode assembly to contact the subject directly. In this set of preferred embodiments, standard silver/silver chloride gel electrodes are employed. The substrate with the electrode pads can be disposed of after use according to health and safety regulations, while the data processing means can be re-used with a new substrate and pair of pads to form a fresh electrode assembly.

The electrode assembly preferably comprises a pair of electrodes, commonly known as an ECG "lead". Any lead position may be used, depending on the angle at which it is desired to view the heart. In Lead I position, for example, the electrode pair is positioned across the chest from right arm (RA) to left arm (LA) so as to measure the voltage difference between the RA electrode and the LA electrode. However the Applicant has appreciated that electrode assemblies in accordance with the invention may be particularly useful for making multi-lead ECG measurements, for example by affixing two or more of the devices at different lead positions on the body. Thus a Lead II measurement could be made by positioning one device in the right arm (RA) position and another device in the left leg (LL) position, while a Lead III measurement could be made by positioning one device in the left arm (LA) position and another device in the left leg (LL) position. More complex lead positioning, such as 3-lead, 5-lead and 12-lead ECG monitoring, could be carried out using multiple devices. Thus the invention may also extend to a cardiac monitoring system comprising a plurality of the electrode assemblies disclosed herein attached to a subject in different lead positions.

The hybrid nature of the assembly is such that is can be supplied in a sterile state and used by clinical staff in the same way as a single-use electrode assembly, but if collected after use the electrode pads can be discarded while the data processing means is recycled i.e. re-used to make a new electrode assembly. The concept of recycling an electrode assembly is considered novel and inventive in its own right, regardless of whether the assembly has the flexible properties described above, and thus when viewed from a further aspect the present invention provides a method of refurbishing an electrode assembly comprising a substrate, at least two electrodes and self-adhesive means for attaching the assembly to a mammalian subject, wherein the substrate incorporates, sealed within the substrate, data processing means electrically connected to the electrodes, said method comprising the steps of: removing the data processing means from the substrate; discarding the substrate and the electrodes; and incorporating the data processing means into a new substrate so as to form a refurbished electrode assembly.

The invention extends to an electrode assembly for making electrocardiogram measurements comprising a substrate and at least two electrodes, the substrate comprising at least one electronic item sealed therewithin and being adapted to facilitate removal of said electronic item from the substrate prior to disposal of the substrate.

The electronic item could be a battery, data processor, printed circuit board or any other electronic item. Of course more than one such electronic item might be removable. The substrate could be adapted to facilitate removal of the electronic item(s) by being a laminated structure, as described elsewhere herein, optionally with a line or zone of weakness to facilitate rupture or tearing. A frangible or otherwise breakable electrical connection between the substrate and the removable electronic item may be provided.

Thus it will be understood that in accordance with these aspects of the invention a given electrode assembly may incorporate a recycled i.e. re-used data processing means or other electronic item(s). This prevents unnecessary waste and reduces the amount of medical waste sent to landfill. Such refurbishment represents a marked deviation as the electrode assemblies that are currently used are designated for single use and then disposed of as a whole. In a preferred set of embodiments, a battery associated with the data processor may be recharged or replaced before forming the refurbished assembly. All of the components may be cleaned/sterilised before being incorporated into a new substrate. Preferably the data processing means is sealed into the substrate so that the assembly can be provided in a sterile state ready for medical use. Clinical staff can simply apply a refurbished assembly in the same way as a single-use one.

Refurbishment can be facilitated by using a substrate comprising a laminated structure, with the data processing means embedded between a pair of layers above. As is described above, one or more extendible connections and/or a flexible substrate may be provided. Accordingly any of the features described above with respect to the first aspect of the invention may equally be employed when refurbishing an electrode assembly.

It has further been appreciated that the concept of removing and re-using an electronic item, while the rest of the assembly which has been in contact with a subject is discarded for hygiene purposes, may find application in health monitoring devices other than those making cardiac measurements. Various types of sensor may be provided by a wearable assembly and connected to an electronic item therein that facilitates collection and/or transmission of date from the sensor(s). Thus, when viewed from a further aspect the present invention provides a sensor assembly for monitoring a mammalian subject, the assembly comprising a wearable substrate, at least one sensor arranged to detect a bodily function, and an electronic item arranged to store and/or process data received from the sensor, the electronic item being sealed within the substrate and the substrate being adapted to facilitate removal of said electronic item from the substrate prior to disposal of the substrate.

The electronic item may comprise one or more of: a data processor, electronic memory, wireless transmitter, battery, printed circuit board, or any other signal handling circuitry for the sensor(s). The sensor(s) may be integrated with the electronic item or arranged separately. The electronic item may be electrically or wirelessly connected to the sensor(s). Where an electrical connection is provided then it may be an extendible connection of the type described above.

As is discussed above, such a sensor assembly can be at least partially recycled after use, with the substrate disposed of as medical waste while the electronic item(s) are reclaimed for re-use. Preferably an electronic memory can be cleared before re-use. In order to increase the re-usabilty of the electronic item(s) in the manufacture of new sensor assemblies, it is preferable that a data processor can be re-programmed for re-use. This is a particularly beneficial feature as it enables the same piece of hardware to be used with different types of sensor. Furthermore, the data processor is preferably programmable or re-programmable to run a data processing method specific to a particular sensor and/or a particular application. This means that each processor can be programmed during assembly to provide a sensing device having a desired functionality. Such a feature can provide benefits for a data processing means in an electrode assembly for ECG measurements and may therefore be combined with any of the earlier described embodiments.

The sensor(s) may be adapted to detect one or more bodily functions, including (but not limited to) cardiac rhythm, respiration, movement, temperature, etc. In one set of embodiments the sensor(s) may be arranged at least in partial contact with the skin of a subject, the contact being electrical and/or physical. The sensor is preferably not invasive. Such a sensor is preferably designed for use with a single subject and may therefore be discarded, together with the worn substrate, after use. The sensor may comprise a pair of ECG electrodes and have some of the features described above. In another set of embodiments the sensor(s) may not require direct contact with a subject and thus may also be re-used without risk of cross-contamination. In such embodiments it is preferable that the at least one sensor is also sealed within the substrate and can be removed prior to disposal. In order facilitate removal of items from the substrate, it may have a laminated structure and any of the features already described hereinabove.

It will be appreciated that in any given sensor assembly, one or more electronic items and potentially also the sensor(s) may be re-used having been reclaimed from another device at the end of its life. The refurbishment method outlined above therefore also extends to the manufacture of sensor assemblies beyond electrode assemblies e.g. for taking ECG measurements.

When viewed from a yet further aspect the present invention provides a method of refurbishing a sensor assembly comprising a wearable substrate, at least one sensor arranged to detect a bodily function, and an electronic item arranged to store and/or process data received from the sensor, wherein the electronic item is sealed within the substrate, said method comprising the steps of: removing the electronic item from the substrate; discarding the substrate; and incorporating the electronic item into a new substrate so as to form a refurbished sensor assembly. Preferably the electronic item is sealed into a laminated structure in the refurbished sensor assembly. As is described above, the sensor(s) may also be sealed within the substrate and in such embodiments the method includes removal of the sensor(s) as well as the electronic item and re-use of the sensor(s) in a refurbished sensor assembly. The re-used sensor(s) may be incorporated either internally or externally in the refurbished sensor assembly.

Whether manufacturing a sensor or electrode assembly from new components or from re-used items, it has been recognised that the manufacturing process can be simplified when it is reduced to a relatively small number of easily reproduced steps. Ease of manufacture can be enabled by a laminated structure. In its simplest form a laminated device need only be assembled from three groups of components, namely: a body side substrate layer (and e.g. any associated components arranged to be in contact with a subject's body); internal components e.g. one or more electronic items; and a top side substrate layer (and e.g. any associated components arranged to be visible during use). Preferably at least one of the substrate layers is provided with self-adhesive means on an inner surface. This means that the laminated structure can seal itself as soon as the components are assembled between the two layers.

The invention extends to another aspect wherein a method of manufacturing a wearable sensor assembly for monitoring a mammalian subject comprises the steps of: providing a first (e.g. body side) substrate layer, a second (e.g. top side) substrate layer and at least one electronic item connected to a sensor that is arranged to detect a bodily function, at least one of the substrate layers being provided with self-adhesive means; placing the at least one electronic item between the first and second substrate layers in contact with the self-adhesive means; and sealing the first and second substrate layers together with the electronic item sandwiched therebetween.

The benefits of such a manufacturing method are twofold. Firstly, it means that the core of a device can be assembled relatively quickly in a small number of steps. Manual assembly is simplified, which can be an important consideration when re-using electronic items as it may be desirable for a human to check each item e.g. to verify that it has been cleaned and/or carries an ID to enable tracking through one or more refurbishment cycles. Secondly, the laminated structure of the assembly means that the electronic item is safely sealed from the external environment during use but can be reclaimed by separating the substrate layers, which are preferably disposable, after use. Typically the electronic item (and potentially any sensor(s) also sealed in the assembly) represents the highest cost component in the assembly. Using this method to manufacture assemblies from new and re-used electronic items therefore reduces the material waste and costs usually associated with single-use medical equipment.

At least one of the substrate layers is provided with self-adhesive means and preferably both of the layers each have self-adhesive means on an inner surface, so that the electronic item and anything else sandwiched between the layers is adhered on both sides. The self-adhesive means preferably comprises an adhesive coating on the surface of the substrate layer. The substrate layers can conveniently be cut from a pre-coated sheet of material. So as to facilitate handling of the layers, the adhesive coating is preferably provided with a removable outer cover, such as a peelable cover sheet, that can be removed to expose the adhesive coating on the surface. The removable cover can also help to improve ease of assembly.

In a preferred set of embodiments the removable cover is cut into a number of pre-defined areas. This means that part of the cover corresponding to one pre-defined area can be removed independently of part of the cover corresponding to another pre-defined area. Different areas of the adhesive coating can therefore be selectively exposed. This can enable an electronic item (and/or other component) to be adhered to a certain pre-defined area of one of the substrate layers without the risk of accidental adhesion to another part of the assembly. Selective removal of different parts of the cover can therefore help with location/alignment of the electronic item (and/or other components) and ensure that it is sealed in a desired position. After placing the electronic item in a desired position as defined by the uncovered area of the surface, another part of the cover can then be removed to expose a pre-defined adhesive area for another electronic item or component and/or to expose an adhesive area to seal directly against the other substrate layer. Preferably the removable cover is kiss cut or face cut so that the underlying substrate layer remains intact.

While the self-adhesive means is advantageous in terms of ease of assembly, it is also important for recycling purposes that the layers of the laminated substrate can be separated after they have been sealed together so that the electronic item(s) can be reclaimed after use. However it is not desirable for the assembly to readily delaminate during normal use, so that the electronic item(s) remain safely sealed inside. To facilitate removal of the electronic item(s), at least one (if not both) of the substrate layers may be provided with a line of weakness or other frangible means so that the substrate can be ripped under force. The same effect may be achieved by cutting or rupturing the substrate material in a reclamation step if a frangible means is not provided. The choice of material for the substrate layers can also help. Preferably the substrate layers are formed of a flexible polymeric material, so that they readily flex during use without delaminating, but can be readily torn or split apart if the layer is pierced or cut. A polyurethane foam is one preferred material.

It has further been recognised that it is preferable for the assembly to not only provide for delamination of the substrate layers, but also for ease of removal of the electronic item(s) sealed within the substrate. If an electronic item is sealed directly to the substrate layers that are to be discarded after use then it may not be easy to separate the electronic item from them so that it can be readily re-used. Thus in a preferred set of embodiments the manufacturing method further comprises a step of providing the electronic item(s) with a sacrificial cover before being placed between the substrate layers. The sacrificial cover is preferably arranged to provide a barrier between the electronic item and the self-adhesive means. This means than when the substrate layers are later separated after use, it is the sacrificial cover that is adhered to the layers and can be discarded while the electronic item is free of adhesive. The sacrificial cover may be in the form of a wrapping, pocket, envelope, or the like. Preferably the sacrificial cover is made of a flexible but tearable material, such as e.g. metal foil, polymeric film, polymeric foam, etc. The sacrificial cover may comprise more than one type of material, for example a metal foil layer to minimise electrical interference and a polymeric foam layer to provide cushioning protection.

As is described above, the sensor connected to the electronic item may also be sealed between the substrate layers, i.e. an internal component of the assembly, or it may be at least partially exposed external to the laminated substrate. The (or each) electronic item may of course be connected to more than one sensor. Different sensors may be used to monitor different bodily functions. In one preferred set of embodiments the sensor comprises a pair of ECG electrodes, and the sensor assembly may further comprise any of the preferred features described hereinabove. The connection between the electronic item and the sensor(s) may be an extendible electrical connection of the type described above.

Some preferred features according to all aspects of the invention will now be described.

In a set of embodiments, the electrode or sensor assembly is provided with visual and/or audible user indication means e.g. to indicate when the assembly is operative and/or to indicate malfunction or the mode of operation. In a preferred set of embodiments, a button is provided to allow the user or medical professional to activate the operation of the electrode or sensor assembly. Preferably such a button is sealed within the substrate. This permits battery life to be maximised by powering the device only when it is required.

In some preferred embodiments, other sensors than the ECG electrodes may be provided to give further functionality. For example, an accelerometer and/or magnetometer may be provided which would allow the electrode or sensor assembly to detect motion of the subject. Another, not mutually exclusive, possibility would be to provide an attachment sensor to give an indication of whether or not the assembly is attached, or properly attached, to the subject. This could, for example, prevent activation of the assembly unless such attachment was detected, to avoid operating the device inadvertently or to avoid erroneous results being obtained by operating the device when it is not properly in contact with the subject. In some embodiments, the electrode or sensor assembly could be provided with rewritable memory—e.g. flash memory—in order to allow some degree of re-programming to configure it, to provide software updates etc.

In one beneficial set of embodiments the electrode or sensor assembly comprises a removable identification element bearing information identifying the particular electrode or sensor assembly from which it has been removed. This allows, for example, the identification element to be kept with a patient's notes as a record of the device fitted to the patient which is valuable for audit and checking purposes (since it allows any data records produced by the device to be verified against the identifying information).

Such an arrangement is novel and inventive in its own right and thus when viewed from a further aspect the invention provides an electrode assembly for making electrocardiogram measurements comprising a substrate and at least two electrodes, the assembly further comprising a removable identification element bearing information for identifying the assembly. The invention also extends to a sensor assembly comprising a wearable substrate and at least one sensor arranged to detect a bodily function, the assembly further comprising a removable identification element bearing information for identifying the assembly. Preferably the removable identification element is self-adhesive to allow it easily to be stuck into a set of paper notes. Additionally or alternatively the removable identification element comprises machine-readable identifying information. This could take many forms such as a barcode, radio frequency identification (RFID) chip, magnetically-stored data etc.

In a preferred set of embodiments in which a removable identification element is provided, the electrode or sensor assembly is provided with an indicator which is visible only when the removable identification element is removed. This enables a user, such as a medical professional, to see easily that the device has been used, thereby preventing for example inadvertent re-use of a device.

The device and/or the removable identification element may comprise a writing panel to allow a user manually to record information on it or them—e.g. the patient's name, bed number, ward etc. This may act as useful corroboration of the other records associated with the device.

The removable identification element may take any of a number of different forms. In one set of embodiments it comprises a plastics film attached by adhesive and/or a line of weakness to the electrode or sensor assembly.

In a set of advantageous embodiments the electrode or sensor assembly is configured such that when the removable identification element is removed, the electrode or sensor assembly is activated. This allows easy and intuitive activation of the device by a user and moreover ensures that the identification element is removed, thereby prompting it to be attached to the patient's notes in a preferred set of embodiments. There are a number of ways in which this could be achieved: for example removal of the identification element could release pressure on a micro-switch, expose a light sensor, withdraw an insulating strip from between two sprung contacts etc.

The electrode or sensor assembly itself may be provided with identifying information, either in human-readable form, machine-readable form or both. At least part of this identifying information would typically match the identifying information on the removable element although this is not essential. A benefit of the assembly having its own ID is that it can allow a user to identify, for example, whether the assembly is new or refurbished. In another example such an ID might contain an indication of the presence of reusable or recyclable items inside the assembly. It may be particularly advantageous for the electrode or sensor assembly to carry identifying information relating to an electronic item and other component therein so that when they are re-used they can be tracked from one device to another. This can provide a tracing function during multiple cycles of manufacture and refurbishment. Preferably the identifying information is attached to the electronic item so that the item itself can be tracked when it is removed from one assembly and re-used in the manufacture of another assembly. The ID is preferably unique to the electronic item and stored in read-only format so that it is the same throughout the item's lifetime. The electronic item might be provided with a permanently stored serial number or the like.

BRIEF DESCRIPTION OF THE DRAWINGS

Certain embodiments of the invention will now be described, by way of example only, with reference to the accompanying drawings in which.

DETAILED DESCRIPTION

Figure 1:
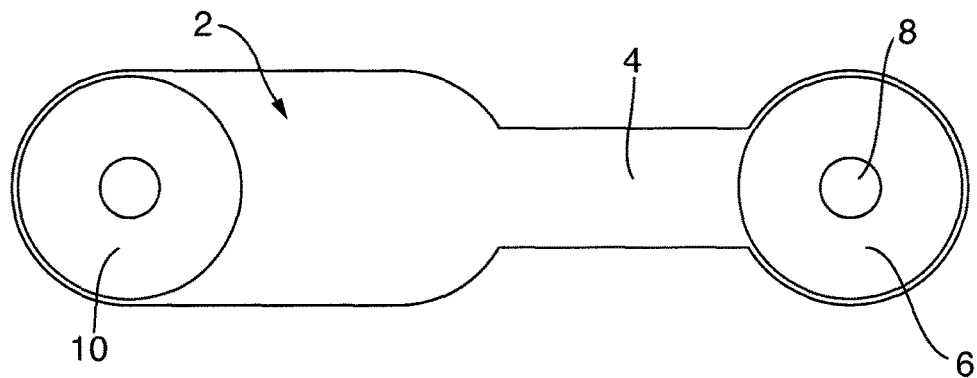
FIG. 1 is a view of an electrode assembly embodying the invention from beneath.
Figure 2:
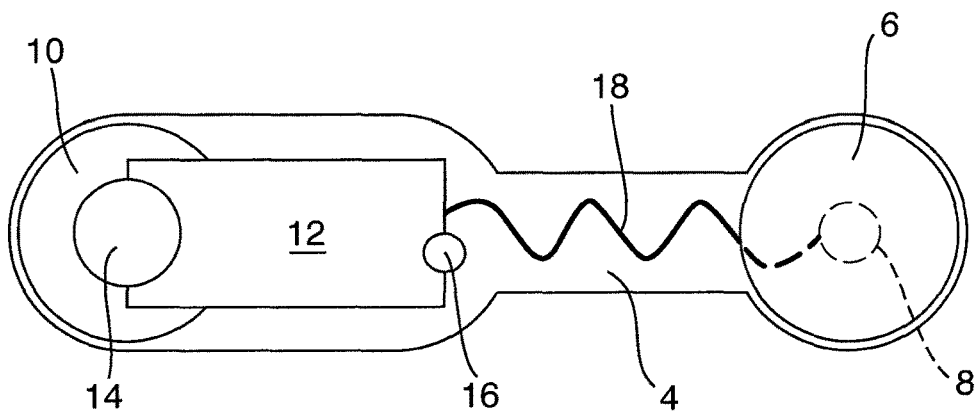
FIG. 2 is a view of the electrode assembly of FIG. 1 from above with the upper layer removed.
Figure 3:
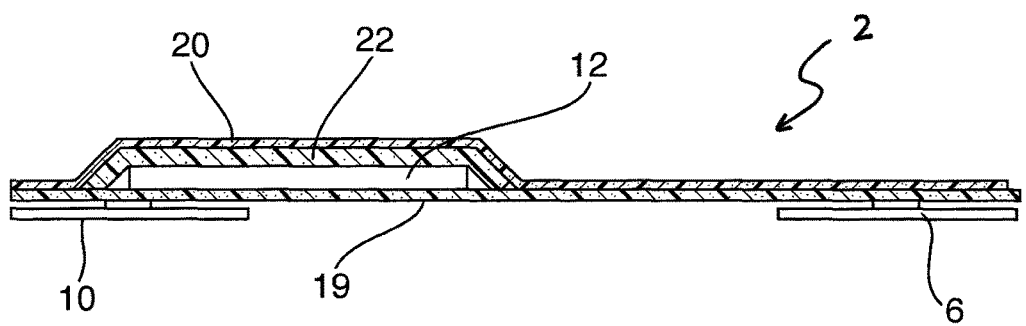
FIG. 3 is a schematic cross-sectional view of the device of FIG. 1.

According to a first embodiment seen in FIGS. 1-3, the electrode assembly is based around a substrate 2 which is, for example, made of a laminate comprising a medical grade polyurethane foam layer on the base onto which is sealed a polyethylene sealing layer (omitted from FIG. 2 for clarity). This construction is seen more clearly in FIG. 3. The substrate has a narrowed portion 4 between the wider part of the substrate and a bulbous end to which is mounted a standard ECG gel electrode module 6, having a central electrically conductive portion 8 surrounded by adhesive. A similar electrode module 10 is provided at the other end of the substrate. The electrode modules 6, 10 are available as standard parts, pre-approved for human medical use. As these are the only parts of the assembly to contact the subject directly, no additional approvals for direct physical contact are required for the rest of the assembly. FIG. 1 shows the body side of the assembly with the self-adhesive electrode pads 6, 10 that contact a subject in use.

Sandwiched between the two layers of the substrate 2 are an electronics module 12, a button cell battery 14, a push button 16 and a connecting wire 18. The connecting wire 18 makes an electrical connection between the conducting portion 8 of the first electrode module 6 and the electronics module 12. It may be seen that the connecting wire 18 has a serpentine shape allowing it easily to extend or contract along the axis of the substrate 2. This allows the whole assembly to be bent or stretched in any direction without causing strain on the electrical connection 18, which could compromise the integrity of the connection or the security of adhesion to the patient's skin. This gives a more reliable electrical signal from the electrode 6 and also enhances the wearer's comfort.

As is seen from FIG. 2, the second electrode module 10 is connected directly to the electronics module 12, as is the button cell battery 14 and the push-button 16. The electronics module 12 is provided on top of the second electrode module 10 so as to improve its mechanical stability. The electronics module 12 includes a microprocessor and a short-range radio transmitter allowing the assembly to transmit data to a suitable receiver. The push-button 16 is of the momentary action type and is arranged initially to apply power from the circuit 12 to initialise it and to maintain the power supply. This allows for long shelf life since the battery 14 is not drained until it is required after being switched on.

FIG. 3 gives a schematic cross-section through the electrode assembly shown in FIGS. 1 and 2. From this it may be seen that the substrate 2 comprises a flexible base layer 19 e.g. of polyurethane foam to which the two standard ECG electrodes 6, 10 are attached. Laminated to the other side of the base layer 19 is a sealing layer 20 of polyurethane foam. An air-tight pocket is formed between the base and sealing layers 19, 20 and this accommodates the electronics module 12 and a further padding layer 22, also of polyurethane foam.

In use the device is switched on by pressing the button 16 and it is then attached to the subject by means of the self-adhesive electrode modules 6, 10. Because the both the electrode modules 6, 10 and the substrate 2 are made of medical grade polyurethane foam, the assembly meets approval for human use. The device is relatively insensitive to its precise placement on the body, although a position that approximates the Lead 1-Left Arm/Right Arm position may be used for the convenience of clinical staff. In one example mode of operation that allows for optimised processing, the device may then periodically transmit data relating to the subject's cardiac rhythm.

Once the electrode assembly is no longer being used for a particular subject, or once the battery 14 is exhausted, the device may be removed and sent for recycling. To recycle the device the two layers 19, 20 are partially separated at the left hand end (as viewed from FIGS. 1 and 2). A line of weakness or other frangible portion may be provided on one or both layers 19, 20 to facilitate this. The battery 14, electronics module 12 and push button 16 may then be removed by pulling them out of the device. Again, a frangible or otherwise separable connect between the electronics module 12 and the electrode module 10 and connecting wire 18 may be provided to facilitate this. Once removed, the battery 14 can be recharged, or recycled using standard facilities, and the electronics module 12 and push button 16 can be re-used in the manufacture of further refurbished devices. The remainder of the device, i.e. the substrate 2 and electrode modules 6, 10 that came into contact with the subject, is disposed of using suitable medical waste protocols. The electronics module 12 and button 16 may be cleaned and sealed inside the two layers of a substrate in a new device, which may then be sterilised ready for re-use.

The description above gives a simple example of a device embodying the invention but is not limiting; many variations are possible. For example, the electronics module may not be provided on top of one of the electrodes but rather adjacent. A further electrical connection, preferably an extendible connection such as a serpentine wire, may then be provided between the electronics module and the other electrode. In another example the device may have more than two electrodes. Multiple extendible electrical connections may be provided so that each of the electrodes is independently connected to the electronics module in a floating manner.

The device could be provided with additional sensors, e.g. one or more accelerometers, contact sensors, temperature sensors etc. to monitor for other vital signs or health functions in addition to cardiac monitoring. Other versions of the device may even use an alternative sensor module to the disclosed ECG electrode modules. The device may therefore be used for health monitoring independently of monitoring cardiac rhythm. A radio transmitter is not essential; data could be stored for later downloading or transmitted by another means.

Figure 4A:
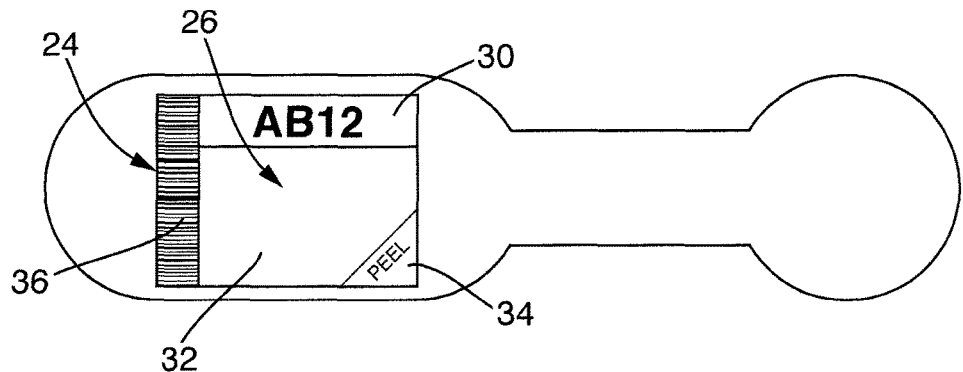
FIG. 4a is a view of another embodiment of the invention with a removable identification label.
Figure 4B:
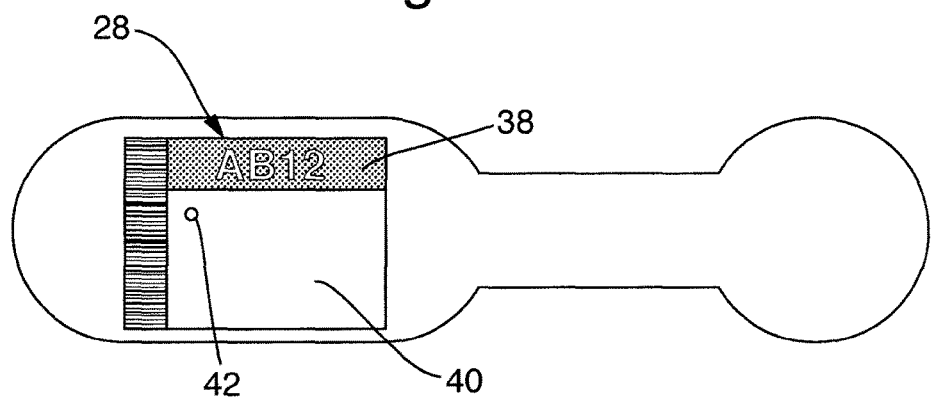
FIG. 4b shows the embodiment of FIG. 4a with the label removed.

A second embodiment of the invention is shown in FIGS. 4a and 4b. This embodiment functions as a wireless ECG monitor in the same way as the previous embodiment and such function will not therefore be repeated. However it differs in that it has a compound label 24. This is made up of a removable self-adhesive label section 26 which is stuck to a permanent portion 28. FIG. 4a shows the removable label section intact 26 and FIG. 4b shows the device with the removable section 26 removed.

The removable label section 26 comprises: a printed information panel 30 bearing identifying information such as a device identification number; a writable panel 32 on which a user can add information such as a patient's name; and an unadhered corner 34 to allow easy removal. It also has a barcode 36 which allows the identification of the device to be read easily by a machine.

Once the removable section 26 is removed it may be placed into the patient's notes as a record of being fitted with the device and to allow any data output subsequently received from it to be matched up. Removing the removable section 26 exposes a second, identical barcode, a second printed information panel 38 and a second writable panel 40. The second information panel 38 has a substantially different background colour to the panel 30 on the removable section 26 so that it may be immediately determined visually by a user that the device has been used. For example it may be red whilst the top panel 30 is white or green.

Also exposed by removing the removable section 26 is a small light sensor 42 beneath a transparent aperture in the writable panel 40. Prior to use this is covered by the opaque writable panel 32 of the removable label section but upon its removal the sensor 42 is subjected to light which may be used to trigger activation of the device (which will then remain activated). Thus intuitive removal of the label automatically activates the device without further action such as pressing a button being required. However other activation means may be provided, for example a pull tab may be removed to connect a battery and power the device. Such a pull tab could be integrated with the label or provided separately, as will be described below.

Figure 5:
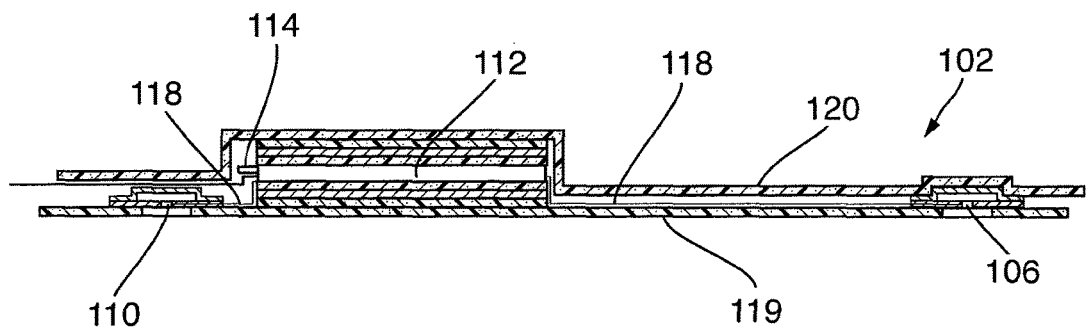
FIG. 5 is a schematic cross-sectional view of a device according to another embodiment of the invention.

FIG. 5 shows a schematic cross-section through the electrode assembly of a device having a slightly different structure. It may be seen that, as before, the substrate 102 comprises two carrier layers 119, 120 e.g. made of polyurethane foam that are laminated together to enclose the functional components of the device, namely a pair of electrode connectors 106, 110, an electronics module 112, an extendible connecting wire 118 and a battery in a holder 114. The device is designed such that assembly can be achieved quickly and easily by hand. Furthermore, after use the functional components can be removed by pulling open the laminated substrate. While the electrode connectors 106, 110 and associated gel pads that have been in physical contact with a patient may be discarded, the battery 115 and electronics module 112 can be re-used or recycled. In particular, a refurbished device can be made by incorporating the electronics module 112 into a new substrate.

With reference to FIGS. 6a-6l there will now be described an exemplary method of making a device as seen in FIG. 5. The same method steps may be used whether manufacturing a device from new functional components or re-using one or more components. The manufacturing method also extends to a sensor assembly without ECG electrodes, but will be described in that context.

Figure 6A:
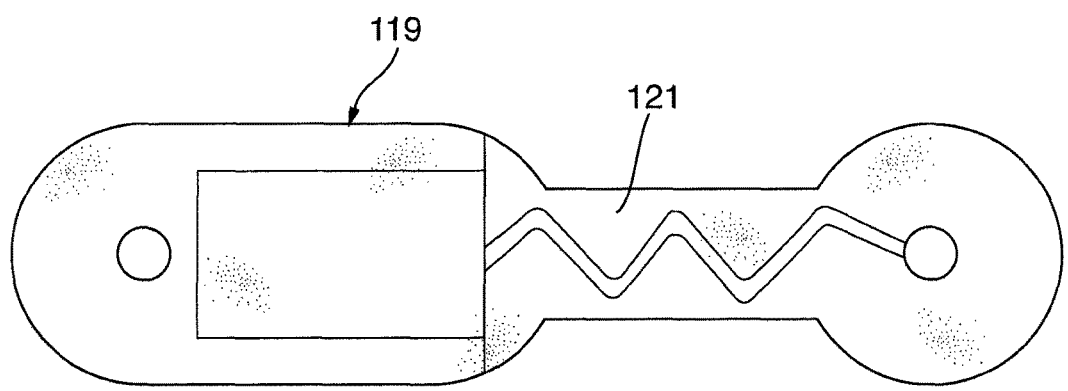
FIGS. 6a-6l illustrate the steps involved in assembling the device seen in FIG. 5.

As is seen in FIG. 6a, the body side carrier layer 119 is cut out from a sheet (e.g. 0.5 mm thick) of stretchable polyurethane foam that has been covered with an adhesive layer and removable cover 121. The other side of the foam layer 119 may be protected by a removable casting paper or other support layer (not shown). The removable cover 121 has a pre-cut outline towards one end of the carrier 119 designed to match an electronics module (rectangular section) and a pre-cut outline across its central portion to match an extendible wire (zig-zag section). The outlines are kiss cut to aid removal of the cover 121.

Figure 6B:
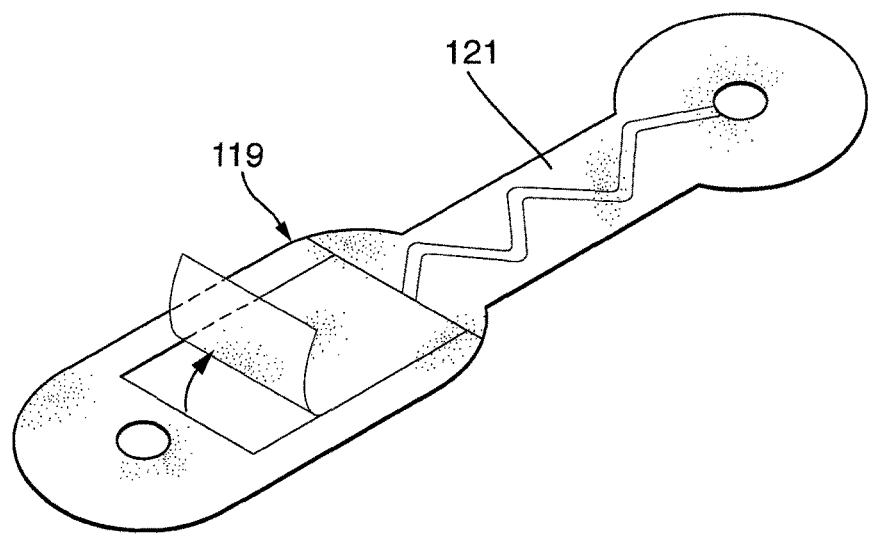

FIG. 6b shows the pre-cut rectangular section of the cover 121 being peeled away to reveal an area of adhesive.

Figure 6C:
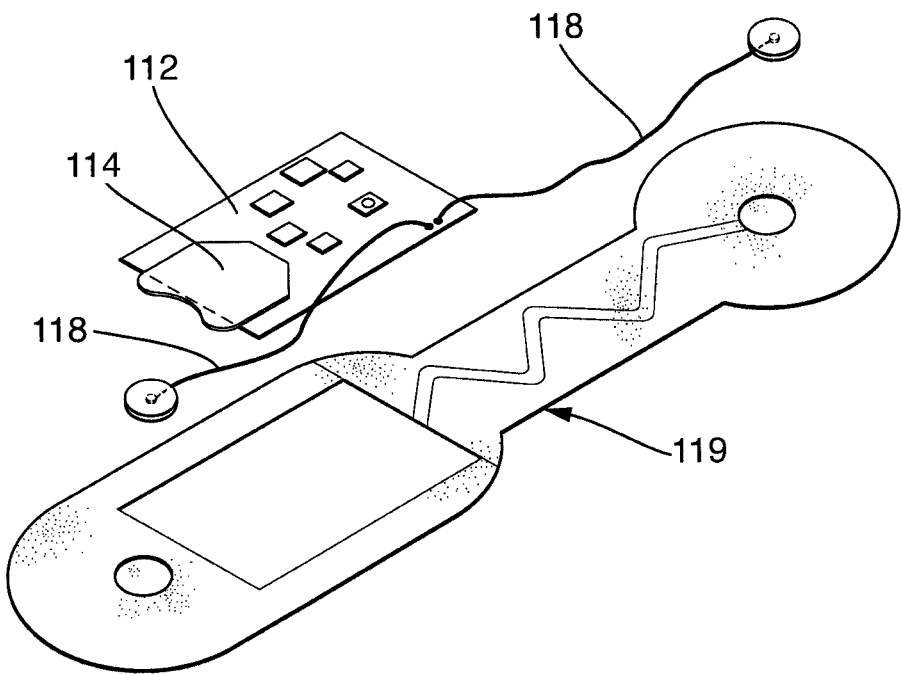

There is seen in FIG. 6c an electronics 112 module, pre-assembled with connecting wires 118 that are soldered to the PCB at one end and to an electrode connector at the other end. Each electrode connector is made by sandwiching a washer between press studs and crimping them together. The washer is a strengthening disc of material having a larger diameter than the clip. The washer may be made of a padding material e.g. 1.0 mm PVC foam or a conductive material. The electronics module 112 includes a processor chip, radio transmitter and battery holder 114.

Figure 6D:
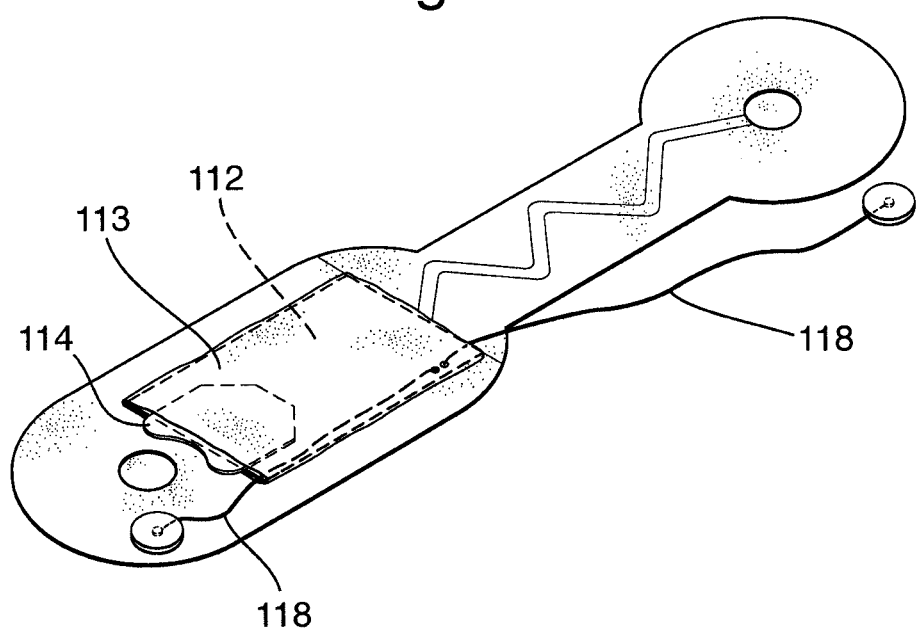

As shown in FIG. 6d, the electronics module 112 (new or re-used) is placed onto the adhesive area. It is important to note that the electronics module 112 is protected by an outer wrap or sleeve 113 e.g. of foam material. A wrapping layer of aluminium foil may also be provided inside the sleeve 113 for immunity to electrostatic discharge. As it is the material of the sleeve 113 that sticks to the adhesive of the carrier layer 119, when the device is opened after use the electronics module 112 can be removed cleanly while the sacrificial sleeve 113 remains attached.

Figure 6E:
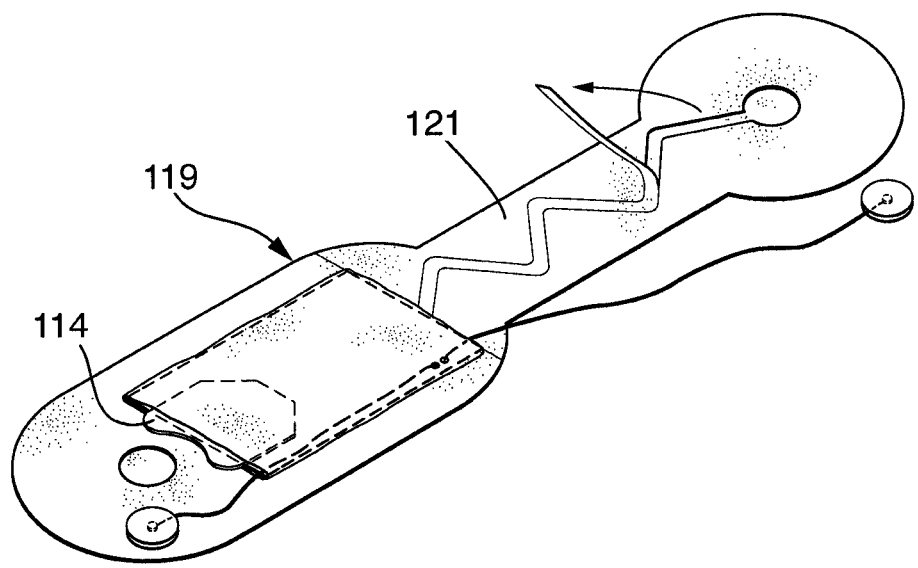

In FIG. 6e the pre-cut zigzag section of the cover 121 is peeled away to reveal another area of adhesive.

Figure 6F:
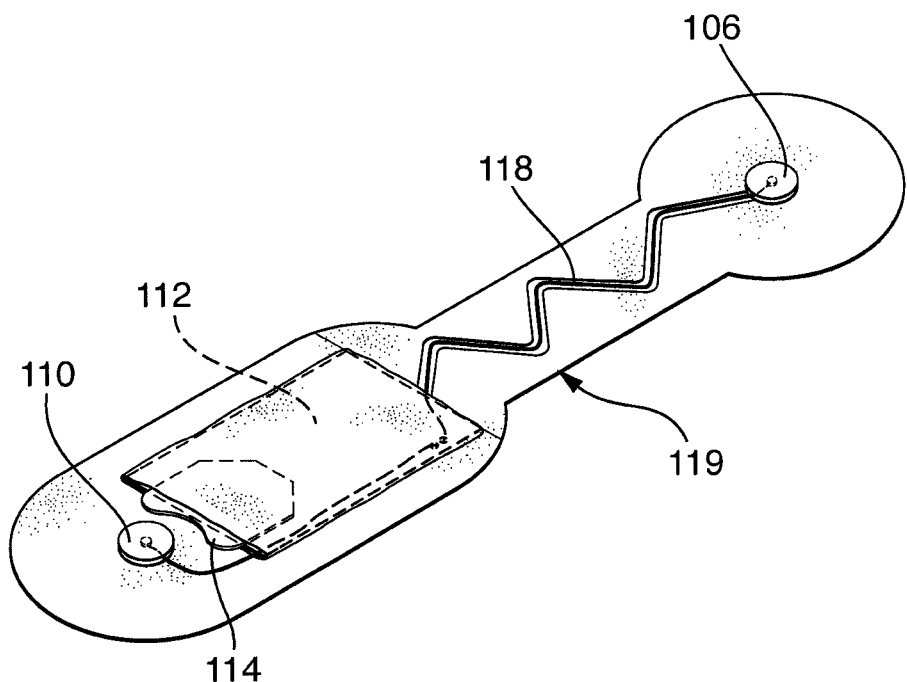

In FIG. 6f the wire 118 connecting the electronics module 112 to the distal electrode clip 106 is positioned over the zigzag area of adhesive. The cut-out in the cover 121 conveniently guides the wire 118 into a meander configuration so that it will be extendible as the stretchable carrier 119 bends and flexes during use. The electrode connector 106 at the end of the wire 118 is positioned over a hole provided at one end of the carrier 119 while the electrode connector 110 adjacent the electronics module 112 is positioned over a hole at the other end. An advantage of the electrode connectors 106, 110 being provided with a washer is that the washer can be adhered to the body side carrier 119. This helps to seal and strengthen the electrode connectors 106, 110. However, it is also possible to omit the washer from the electrode connectors 106, 110 and instead sandwich the carrier layer 119 directly between the press studs and crimp them together. In an alternative method the carrier 119 may therefore be pre-assembled with the electrode connectors 106, 110 before the wire 118 and electronics module 112 are adhesively attached.

Figure 6G:
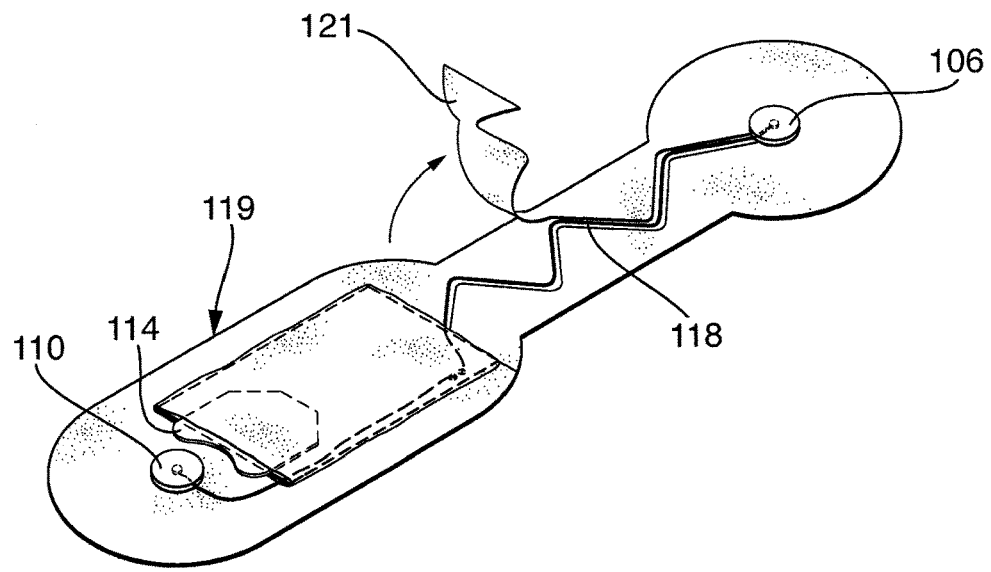

As seen in FIG. 6g the remainder of the covering layer 121 is then removed to expose adhesive regions around the components that have already been affixed.

Figure 6H:
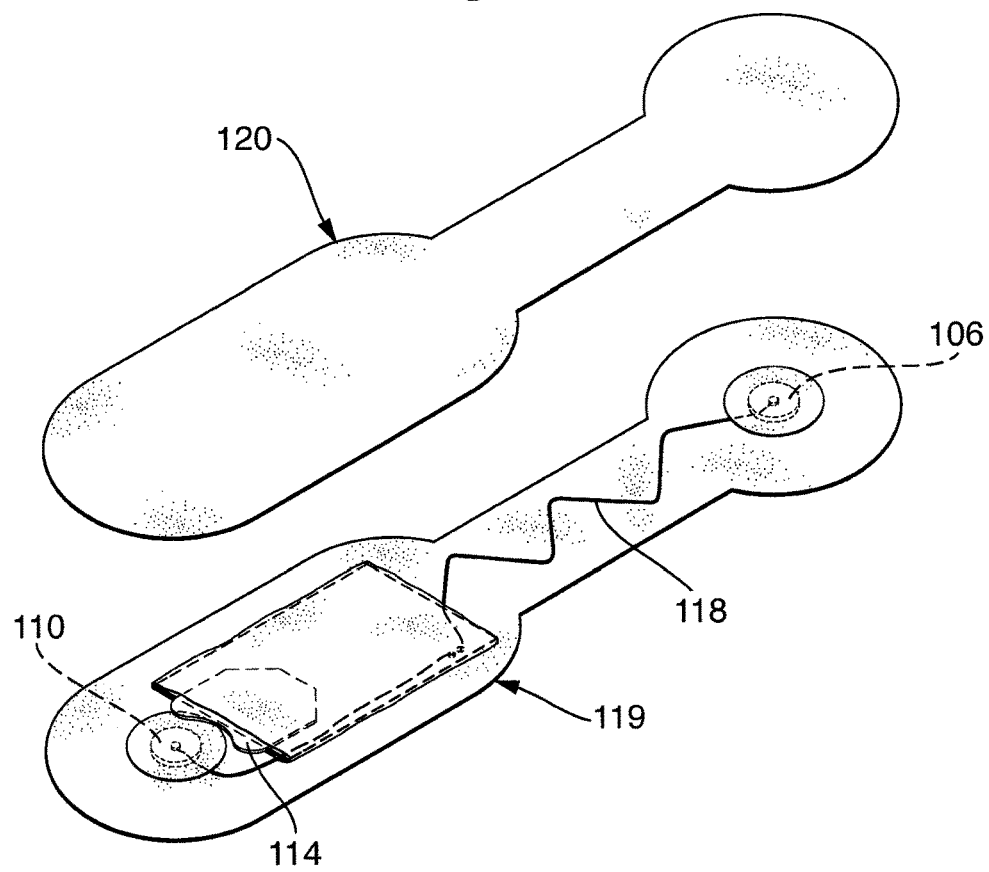

As seen in FIG. 6h a washer disc of thicker foam material (e.g. 1.0 mm thick PU or PVC foam) is placed on top of each of the electrode connectors 106, 110 for sealing and padding purposes. This may be in addition to the washers already crimped into the electrode connectors 106, 110. The top side carrier layer 120, pre-cut or stamped out of a sheet (e.g. 0.5 mm thick) of stretchable polyurethane foam and also provided with a surface layer of adhesive and removable cover layer, can now be placed over the functional components to adhere to the body side carrier 119. Again, the outer surface of the carrier layer 120 may be protected by a casting paper or other removable support material.

Figure 6I:
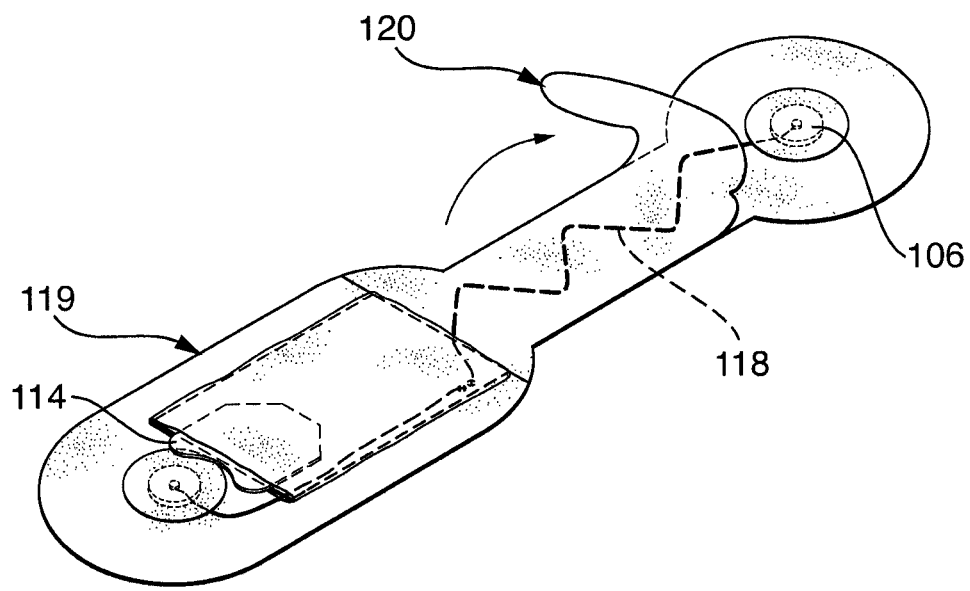

FIG. 6i shows the top carrier 120 fitting over the wire 118 and electrode clip 106 at one end of the assembly so that these components are laminated inside the assembled substrate 102. Lamination is assisted by the cover layer of the top carrier 120 being cut into multiple e.g. two or three sections along its length that can be peeled off separately. The right hand section of the cover layer is removed first so that the layers 119, 120 can be sealed together at this end of the assembly.

Figure 6J:
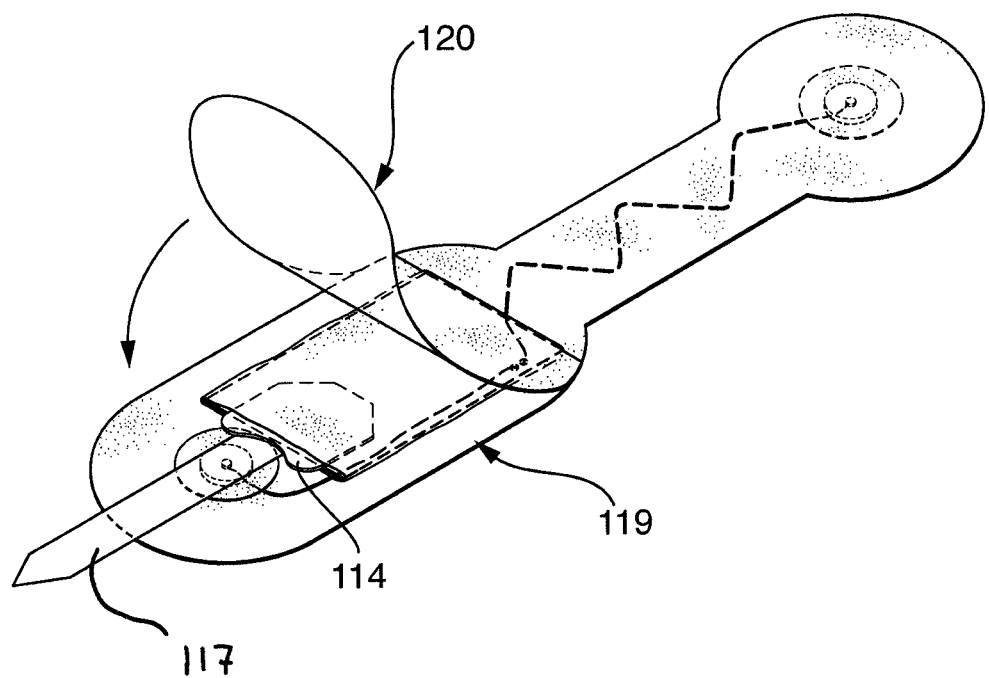

As is seen in FIG. 6j, a pull tab 117 is inserted into the battery holder 114 before fitting the battery 115 (seen in FIG. 6k), so that power is not drained until the assembly is made into a device and activated. The pull tab 117 can be made of silicone or another low-adhesion material so that it can be pulled out easily from between the layers 119, 120. The left hand section of the cover layer over the adhesive coating on the top carrier 120 can now be removed.

Figure 6K:
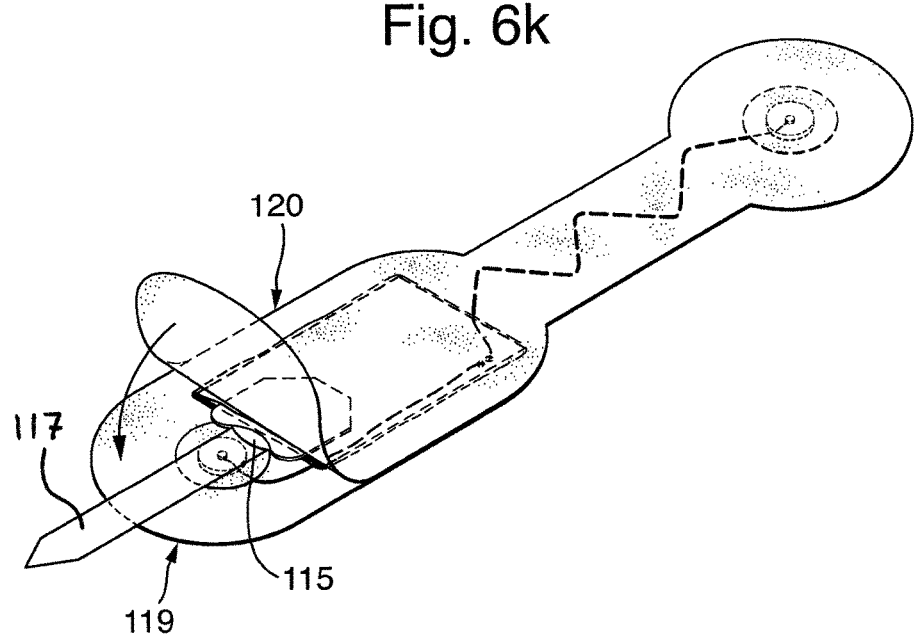

There is seen in FIG. 6k a button cell 115 inserted into the holder 114 on top of the pull tab 117. In a final assembly step, the top carrier 120 covers over the last of the components to seal closed the substrate assembly 102. Care is taken to ensure a good seal at the edges.

Figure 6L:
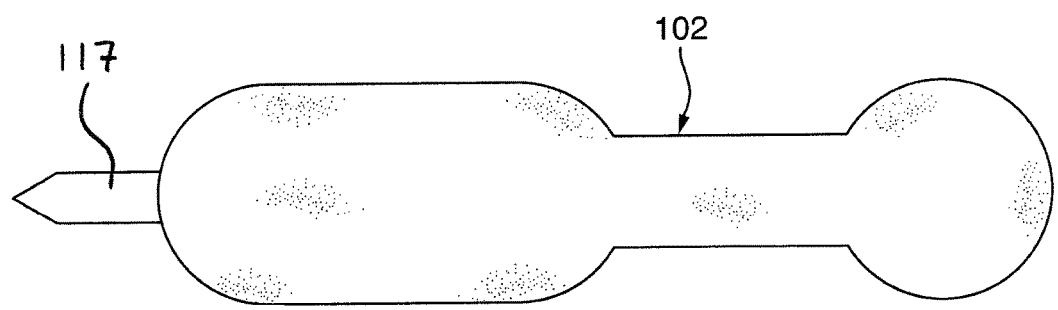

FIG. 6l shows the laminated assembly 102, which is now ready to be packaged as a device. The substrate layers 119, 120 are sealed together with only the pull tab 117 protruding, which can later be removed to activate the battery. Standard ECG gel electrodes having a male press stud connector can be attached to the female electrode connectors 106, 110 on the body side. Any protective covers on the outside of the foam layers 119, 120, such as a casting paper, can now be removed. A label as described above with respect to FIG. 4 may be applied to the top side of the substrate 102. The label may assign a unique device ID number.

To refurbish the components of a device after use, the substrate 2, 102 is sent to a dedicated processing facility where the two layers are separated so that the battery and electronics module, or at least its PCB, can be removed. The processor chip on the PCB has an internally programmed ID number that is unique to that electronics module throughout its lifetime. This ensures that each chip can be traced even though it may be assigned a new device ID number when assembled into a new device. By checking the chip ID against records it can be ensured that re-use is monitored and regulated. Before the electronics module is re-used it may be re-programmed, for example for a different application or even for use with sensors other than the electrodes described above.

While some preferred embodiments have been described above in the context of an assembly suitable to carry ECG electrodes, it will be understood that such an assembly, in particular an assembly having a laminated structure, can provide benefits regardless of the type of sensor. Thus the electrode connectors may be used to mount a sensor other than an ECG gel electrode, such as a temperature or movement sensor. Accordingly the same assembly structure may be used to monitor for other vital signs or health functions instead of (or in addition to) cardiac monitoring. Advantageously the electronics module can be removed after use of a particular device, optionally re-programmed, and incorporated into a new assembly providing the same or a different sensing function.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A method of refurbishing a sensor assembly comprising a wearable substrate, at least one sensor arranged to detect a bodily function, the sensor comprising at least two electrodes disposed on the substrate and an electronic item comprising at least one of a data processor or a wireless transmitter arranged to process or transmit data received from the sensor, wherein the electronic item is sealed within the substrate, said method comprising the steps of:
   removing the electronic item from the substrate;
   discarding the substrate and the electrodes;
   physically cleaning the electronic item;
   incorporating the electronic item into a new substrate so as to form a refurbished sensor assembly having the electronic item sealed within the new substrate; and
   sterilizing the refurbished sensor assembly so that it is placed in a sterile state ready for medical use.

2. The method of claim 1, wherein the substrate comprises a laminated structure which has the electronic item embedded between a pair of layers thereof.

3. The method of claim 1, wherein the electronic item is connected to the electrodes by means of a frangible, or otherwise separable, electrical connection.

4. The method of claim 1, wherein the substrate is provided with a line or zone of weakness to facilitate irreparable rupture of the substrate material to facilitate the removal of the electronic item from the substrate.

5. The method of claim 1, wherein the electronic item further comprises one or more of: a battery a printed circuit board, an electronic memory, a wireless receiver, or data storage.

6. The method of claim 1, wherein the electronic item further includes an electronics module comprising a microprocessor.

7. The method of claim 6, further comprising a step of reprogramming the microprocessor for re-use in the refurbished sensor assembly.

8. The method of claim 1, wherein the sensor assembly further comprises one or more additional sensors.

9. The method of claim 8, wherein the additional sensor(s), or at least an electronic part thereof, is also arranged so as to be removable from the substrate prior to the step of discarding the substrate and the electrodes.

10. The method of claim 1, wherein:
   the sensor assembly further comprises a self-adhesive portion for attaching the assembly to a mammalian subject; and
   the electronic item is a data processor electrically connected to the electrodes.

11. The method of claim 1, wherein the refurbished sensor assembly comprises another sensor arranged to detect a different bodily function.

12. The method of claim 1, wherein the refurbished sensor assembly comprises at least two new electrodes.

13. The method of claim 1, wherein the sensor assembly is arranged to make electrocardiogram measurements.

14. The method of claim 1, wherein the electronic item is contained in an air-tight pocket formed by the substrate.

* * * * *